United States Patent [19]

Kohayakawa

[11] 4,252,420

[45] Feb. 24, 1981

[54] OPHTHALMOSCOPICAL APPARATUS PROVIDED WITH ADJUSTMENT SYSTEM

[75] Inventor: Yoshimi Kohayakawa, Yokohama, Japan

[73] Assignee: Canon Kabushiki Kaisha, Tokyo, Japan

[21] Appl. No.: 894,710

[22] Filed: Apr. 10, 1978

[30] Foreign Application Priority Data

Apr. 12, 1977 [JP] Japan .................. 52/41722

[51] Int. Cl.³ .................. A61B 3/14; A61B 3/10; G03B 29/00
[52] U.S. Cl. .................. 351/7; 354/62; 354/13; 354/6
[58] Field of Search .............. 356/153, 399, 4; 351/1, 351/6, 13, 16, 9; 350/2; 354/62

[56] References Cited

U.S. PATENT DOCUMENTS

| | | | |
|---|---|---|---|
| 3,871,772 | 4/1973 | Munnerlyn et al. | 356/153 |
| 3,904,280 | 9/1975 | Tate | 351/1 |
| 4,102,563 | 7/1978 | Matsumura et al. | 351/7 |

FOREIGN PATENT DOCUMENTS 49-103488 9/1974 Japan .
51-330 1/1976 Japan .

*Primary Examiner*—John K. Corbin
*Assistant Examiner*—Rodney B. Bovernick
*Attorney, Agent, or Firm*—Fitzpatrick, Cella, Harper & Scinto

[57] ABSTRACT

An ophthalmoscopical apparatus for carrying out aligning and/or spacing an eye examining instrument is disclosed. The apparatus includes a projection optical system disposed obliquely to the optical axis of the objective lens of the instrument. A beam of infrared light is projected from the projection optical system so as to form an image of indication at a position spaced from the objective lens by a predetermined distance. A beam reflected upon the anterior part of the subject eye is incident on the objective lens and focused on the light receiving surface of an image pick-up tube through an image transmitting system. Thus, an image of the reflected beam is displayed on a screen of cathode ray tube. The examiner adjusts the position of the instrument while observing the image on the cathode ray tube. The adjustment is made in the directions of up-and-down, left-and-right and for-and-back until the image of reflection on the cathode ray tube comes in a predetermined position.

10 Claims, 14 Drawing Figures

OPHTHALMOSCOPICAL APPARATUS PROVIDED WITH ADJUSTMENT SYSTEM

BACKGROUND OF THE INVENTION

1. Field of the Invention

The present invention relates to ophthalmic instruments for examining and testing eyes.

2. Description of the Prior Art

For carrying out examination or photography of an eye it is very important to preliminarily position the appropriate instrument correctly relative to the subject eye. For example, in setting a retinal camera there are required two kinds of adjustments. Initially, the camera must be adjusted vertically (up-and-down) and horizontally (left-and-right), while observing the subject eye from the side of the camera, to a position at which the illumination light emerging from the objective lens is properly incident upon the pupil of the subject eye. This kind of adjustment is usually called "alignment". Secondly, while viewing an image of the fundus of the subject eye through the finder, the camera is adjusted by moving it forwards or backward to a position at which the image of the fundus becomes clearly visible. In the art, this kind of adjustment is generally called "adjustment of working distance".

For ophthalmoscopy there are known such type of instruments in which infrared light is used in examining the subject eye or in illuminating the fundus for focusing. The iris of the eye is not sensitive to infrared light and therefore no constriction of the pupil is caused by illumination with infrared light. Accordingly, the use of infrared light has an advantage in that it permits examining, measuring, testing or photographing of the eye in a state of spontaneous dilatation.

However, the illumination light of infrared rays is not visible. Therefore, the adjustment of such type of apparatus must be made by relying upon only the examiner's sense or skillfulness. Also, the image formed with infrared light must be converted into a visible image for observation by using an infrared converter because no infrared image is visible to the naked eye. By this conversion, however the quality of the image is reduced to the extent that the visible image is not longer useful for the adjustment of working distance. If a photograph of the fundus is taken under the condition of insufficiently adjusted working distance, then there will be produced a defective image which is damaged by a portion of fundus illuminating light reflected upon the cornea and then introduced into the film. In measuring the eye, such insufficient adjustment of working distance will cause measuring error to be increased.

U.S. Pat. No. 3,871,772 has disclosed an eye examining instrument which enables one to carry out not only alignment but also working distance adjustment. But, the finder belonging to the instrument can not be used to effect observation during adjustment. The apparatus disclosed therein is provided with a separate finder as the observation finder for adjustment.

SUMMARY OF THE INVENTION

Accordingly, it is an object of the invention to provide an ophthalmoscopic apparatus which permits correct adjustment of the working distance between the eye examining instrument and the subject eye.

It is another object of the invention to provide an ophthalmoscopic apparatus which permits attainment of correct alignment of the instrument and the eye.

A further object of the invention is to provide an ophthalmoscopic apparatus in which the adjustment of working distance or alignment can be effected by forming a bright point in the anterior part of the eye or a dark point in a light background and observing the bright or dark point thus formed.

Still a further object of the invention is to provide an ophthalmoscopic apparatus in which the observation for adjustment can be effected making use of observing means belonging to the eye examining instrument.

After the adjustments of alignment and working distance of the eye examining instrument, an accurate focusing is carried out. During focusing there is often caused change in working distance. Therefore, it is desirable that the view field of the part to be examined such as fundus of eye and the view field of the anterior part of the eye for adjustment can be observed at the same time or changing-over of these two view fields can be done instantly. By doing so, it becomes possible to carry out both the adjustment of working distance and the focusing almost simultaneously.

Other and further objects, features and advantages of the invention will appear more fully from the following description.

DESCRIPTION OF THE PREFERRED EMBODIMENTS

Figure 1:
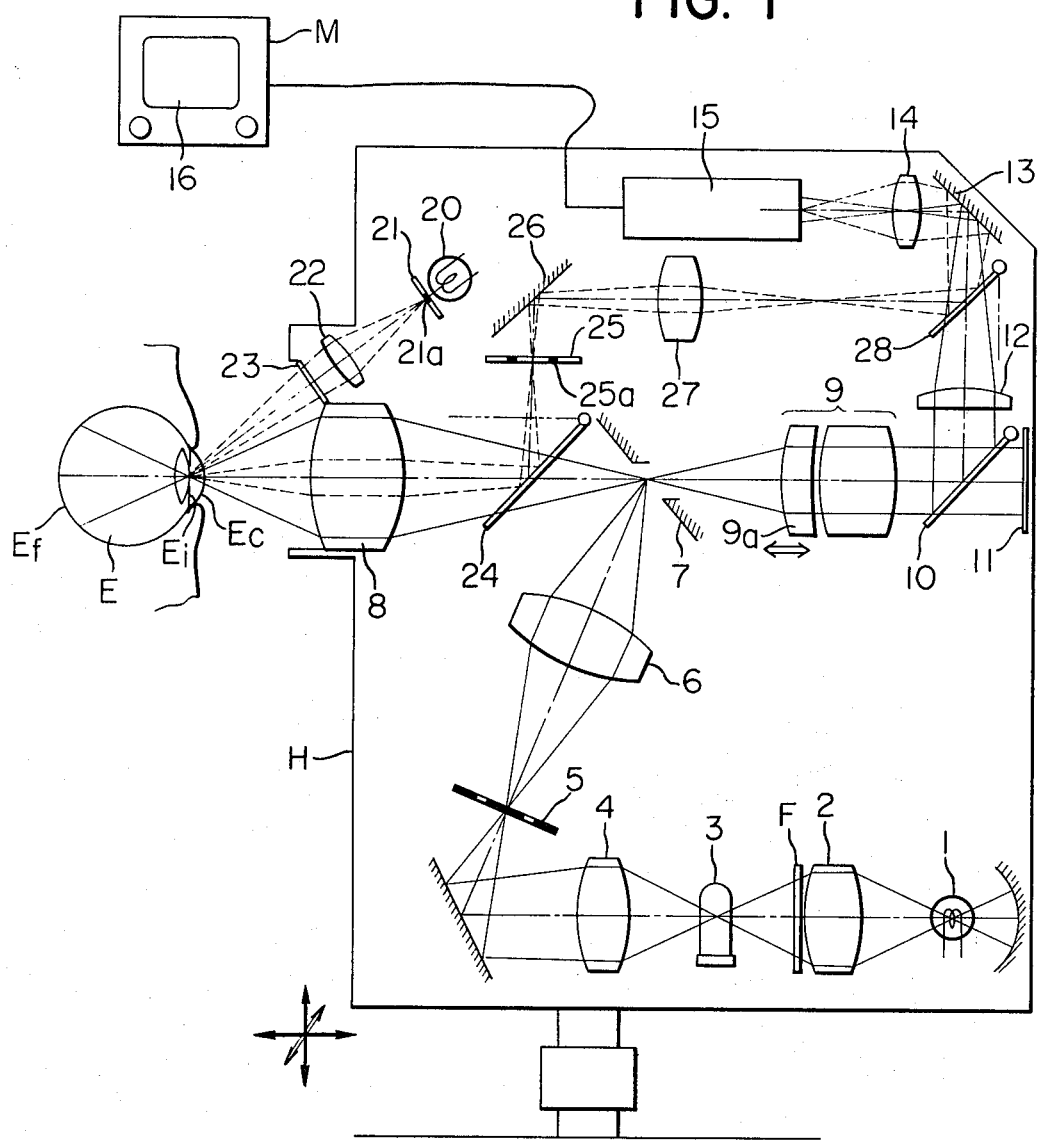
FIG. 1 is a schematic vertical section showing an embodiment of the present invention.
Figure 2:
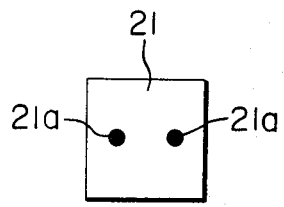
FIG. 2 is a plan view of the chart used in the embodiment as a member of the apparatus.

Referring to FIGS. 1-4, there is shown an embodiment of the present invention. In FIG. 1, E is an eye to be examined, Ec is the cornea of the eye, Ei is the iris of the eye and Ef is the fundus of the eye. The face of the examinee is unmovable, supported by a chin holder not shown.

H designates the housing of a retinal camera for fundus photographing. 1 is an incandescent lamp, 2 is a condenser lens, 3 is a strobo tube and 4 is a further condenser lens. The incandescent lamp 1 and the strobo tube 3 are conjugate relative to the condenser lens 2. F designates a filter which reflects visible rays and transmits infrared rays. The beam of light emitted from the lamp 1 is filtered by the filter F to select only infrared or near infrared rays which do not contract the pupil.

The reference numeral 5 designates a ring slit which forms a corona at the anterior eye portion near to the cornea or the iris of the eye to illuminate thereby the fundus through the pupil. The ring slit 5 and the strobo tube 3 are disposed conjugate relative to the condenser lens 4. The reference numeral 6 is a projection lens which forms an image of the ring slit illuminated by strobo light or infrared beam on a mirror with opening 7.

8 is an objective opposed to the eye E so as to form an image of the fundus Ef. A relay lens 8 reforms on a film 11 the fundus image formed by the objective 8. A portion 9a of the relay lens 9 is movable in the direction of optical axis and is used for focusing.

In addition to the formation of the fundus image, the above described objective 8 has another function to reform the image of the ring slit 5 formed on the bored mirror 7 in the anterior eye part. The beam reflected upon the fundus emerges from the subject eye passing through the dark portion in the center of corona image of the ring slit. When the beam emerged from the eye is directed to the film 11 through the objective 8 and the relay lens 9, the opening of the mirror 7 shuts out light rays other than the fundus photographing beam in the known manner.

10 is a flap mirror, 12 is a field lens and 13 is a light path switching mirror. The field lens 12 and the film 11 are conjugate relative to the mirror surface. On the field lens there is formed an aerial image of the fundus of the eye which is focused on the light receiving surface of an image pick-up tube for infrared ray 15 by a lens 14. A display apparatus M comprises a cathode ray tube 16 an electric processing system not shown.

Now, a detailed description is made of the indication projection part and the observing system provided for adjustment of working distance.

Figure 4:
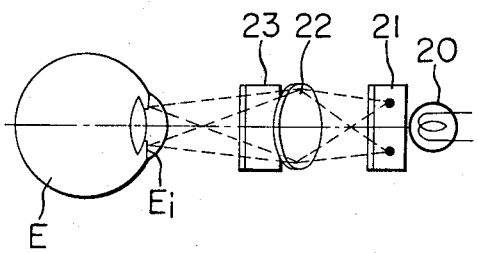
FIG. 4 is a partial plan view of the apparatus shown in FIG. 1.

For working distance adjustment, there are provided an incandescent lamp 20, a chart 21, a projection lens 22 and an infrared ray transmitting filter 23. As seen best from FIG. 2, the chart 21 has two shade points 21a horizontally disposed thereon. Relative to the projection lens 22, the chart 21 and the position which a predetermined part on the iris Ei has to take are conjugate. In the shown embodiment, the position mentioned above is a point lying on the intersectional line of a plane which the iris in a predetermined position makes and a horizontal plane containing the center axis of the pupil and also on the iris in the state of spontaneous dilatation. FIG. 4 is a top view of these members 20–23 and the subject eye E.

Figure 3:
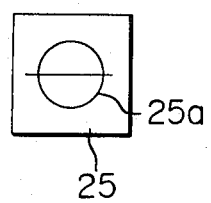
FIG. 3 shows another form of chart used in the invention.
Figure 6:
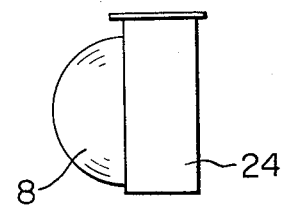
FIG. 6 shows a flap mirror and an objective as viewed from the image space side.
Figure 7:
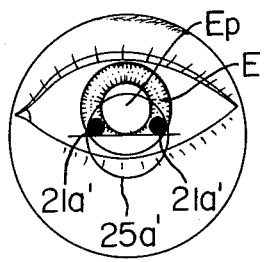
FIGS. 7 through 10 illustrate various observation view fields.
Figure 8:
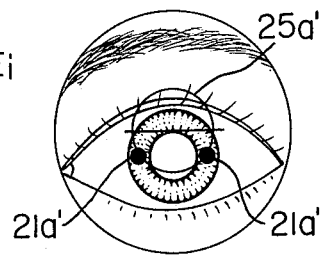

Between the objective 8 and the mirror with opening 7 there is interposed a flap mirror 24. The reference numeral 25 designates a chart which has, as shown in FIG. 3, a mark 25a consisting of a circle and a straight line extending through the center of the circle. The chart 25 and the iris Ei are conjugate relative to the objective 8 and to the surface of the mirror 24, and the center of the marked circle is coincident with the optical axis. 26 is an optical path switching mirror, 27 is a relay lens and 28 is a flap mirror. The image of iris(-pupil) formed on the chart 25 is once focused by the relay lens 27 and thereafter it is focused on the light receiving surface of the image pick-up tube 15 through the mirrors 28 and 13 and the lens 14. As the flap mirrors 24 and 28 there may be used also such partial reflection mirror that has a reflecting surface only on the left or right side half of it, as viewed from the optical axis, as shown in FIG. 6. In this case, the fundus and the anterior part of the eye can be dislayed on the display tube at the right and left sides thereof at the same time respectively. Housing H is supported for up-and-down, right-and-leftward and for-and-backward movements. Supporting mechanism for this purpose is well known and therefore no further description thereof is necessary.

The manner of operation of the above described apparatus is as follows:

Prior to beginning examining eye, the examinee is introduced into a dark room to spontaneously dilate the eye to be examined.

Initially the flap mirrors 24 and 28 are placed obliquely as illustrated in FIG. 1 and the image pick-up tube 15 and the display apparatus M are brought into operation preliminarily. Thereafter, the examiner puts on the incandescent lamp 20 to illuminate the chart 21. The beam of light passed through the chart 21 is converged by the projection lens 22 and only the beam of infrared rays is taken up through the filter 23 so that at a predetermined position there is formed an image of the shade points (indication mark) 21a. On the other hand, the infrared beam emerged from the filter 23 illuminates the anterior eye part. As a result, there are displayed on the catholde ray tube 16 of the display apparatus such images as illustrated in FIGS. 7-10. In these figures, 21a' is an image of the shade point 21a. Also, 25a is the mark provided on the chart 25, Ei is the iris and Ep is the pupil. Since the center of the circle of the mark 25a is coincident with the optical axis of the objective 8 as mentioned above, any deviation in position between the circle and the pupil Ep appearing on the display apparatus as in the case of FIG. 7 or 8 indicates that the objective is in a wrong position deviated vertically with respect to the eye.

Figure 9:
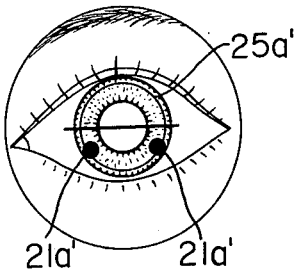
Figure 10:
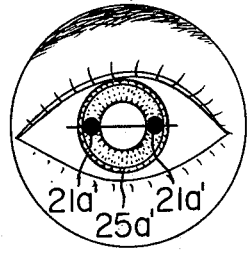

To correct such a deviation of the objective in the vertical direction, the housing H must be moved as whole upwardly or downwardly to the position at which the pupil Ep comes into the center of the circle of the mark 25a as illustrated in FIG. 9 or 10. Also, an adjustment for alignment in the horizontal (rightwards or leftwards) direction is made in a similar manner if necessary.

After adjustment for alignment in vertical and/or horizontal direction has been made, a further adjustment must be made for the distance between the subject eye and the objective. This adjustment of working distance can be effected making use of the image 21a' of the shade points. The reason why the image of the shade points becomes visible through the objective is that the iris of the eye has an effect similar to a diffusing surface and can scatter the incident beam.

Figure 5:
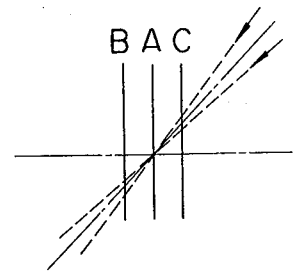
FIG. 5 is an explanatory view for explaining the optical function.

In FIG. 5 the broken line indicates the beam by which an image of the shade points 21a is formed and the plane A is a predetermined reference plane. If the position of the iris is coincident with the plane B, then the beam will be reflected by the iris at the side under the horizontal plane containing the center of the pupil. If the position of the iris is in the plane C, then the beam will be reflected by the iris at the upper side. Therefore, the amount and the direction of the deviation from the reference distance can be known by observing whether the image of the shade points lies above or under the horizontal plane. While the image becomes dim a little at the plane of B or C, it is of no significance since the distance from the plane A to the plane B or C is very small. In case of FIG. 7, the image 21a' of the shade points is found to be above the straight line of the chart 25, which means that the distance between the subject eye and the objective is too short. On the contrary, FIG. 8 or 9 wherein the image 21a' lies under the straight mark line shows the case where the distance between the eye and the objective is too long. To obtain the proper working distance, the examiner moves the housing H forward or backward to the position at which the shade point's image 21a' and the mark line of the indication mark 25a are in an overlapped relation. In this manner, an adjustment of working distance is made correctly. When all the adjustments are completed in vertical, horizontal and for-and-backward directions, there is displayed on the cathode ray tube an image as illustrated in FIG. 10.

While in the above described embodiment, two indications are used for alignment, only one indication may be used for this purpose. Also, the indication mark may be projected on the sclera.

After the completion of the necessary adjustment, the flap mirror 24 is swung into its retracted position out of the light path so as to illuminate the fundus with the beam emitted from the lamp 1 and passed through the infrared filter F. The infrared beam reflected upon the fundus of the eye passes through the objective 8, the relay lens 9, the flap mirror 11, the field lens 12, the mirror 13 and the lens 14 in this order and an image of the fundus of the eye is formed on the light receiving surface of the image pick-up tube 15.

The examiner observes the fundus image displayed on the cathode ray tube and carries out focusing while adjusting a part 9a of the relay lens. When it comes in focus, the flap mirror 10 is retracted, the strobo tube 3 is flashed and the shutter (not shown) is released to effect an exposure of the film 11. The flash light emitted from the strobo tube is an ordinary light in the visible range.

Figure 11:
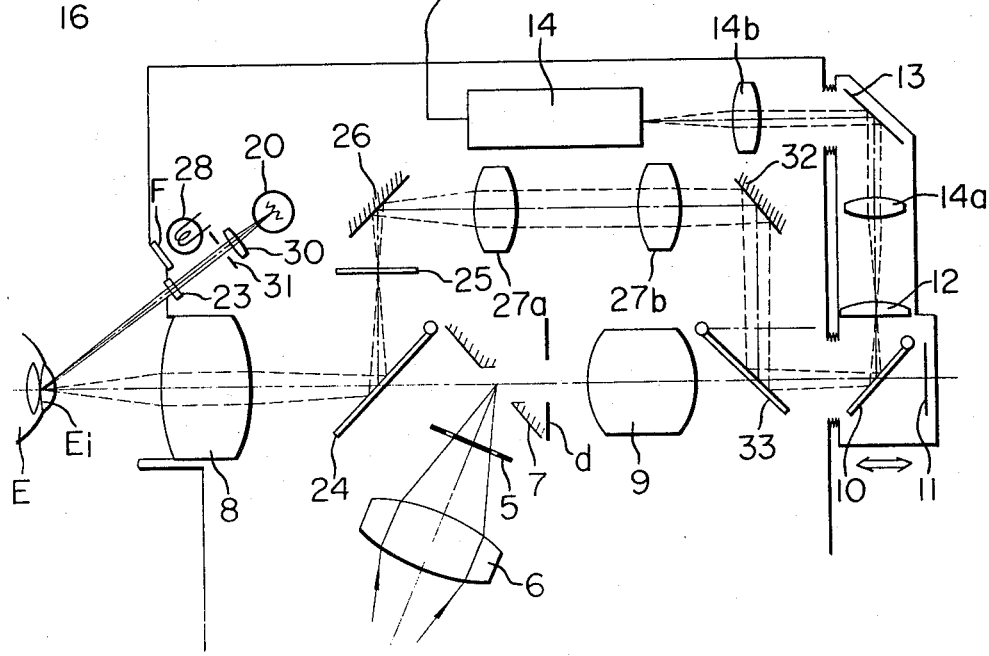
FIG. 11 shows another embodiment of the apparatus according to the invention.

Another embodiment of the present invention is shown in FIG. 11 in which the same members and elements as those in the FIG. 1 embodiment are designated by the same reference numerals and characters as used in FIG. 1. In the embodiment of FIG. 11, the ring slit 5 is positioned in the vicinity of the mirror with opening 7 and a diaphragm d is disposed conjugated to the slit relative to the surface of the mirror 7. The diaphragm d corresponds to the opening of the mirror with opening shown in FIG. 1 in function.

Moreover, in this embodiment, focusing is carried out not by moving the relay lens 9, but by moving all the members of flap mirror 10, film 11, lenses 12 and 14a and mirror 13 as a unit in the direction of the optical axis. The beam travelling from the lens 14a to the lens 14b is a collimated beam. The reference numeral 30 designates a collimator lens. The filament of an incandescent lamp 20 is positioned in the focal point of the collimator lens 30. In front of the collimator lens 30 there is disposed a pin-hole 31 so that a narrow collimated beam is directed to the eye to be examined through an infrared filter 23. After entering the eye, the collimated beam takes the same passage way as in FIG. 1.

Designated by 29 is a light source for illuminating the anterior part of the eye and F is an infrared filter. Here, it should be noted that the intensity of illumination of the collimated beam is higher than that of the light source.

27a and 27b are lenses of which the lens 27a makes the beam exiting from it collimated and the collimated beam is converged by the other lens 27b. The beam emerged from the anterior part of the eye forms an aerial image on the field lens 12 through objective 8, flap mirror 24, chart 25, mirror 26, lenses 27a and 27b, mirror 32 and flap mirrors 33 and 10. Therefore, by switching on the light sources 20 and 29 and also by interposing obliquely the flap mirrors 24 and 33 in a manner as shown in FIG. 11, the examiner can observe on the cathode ray tube 16 images as illustrated in FIGS. 7–10. In the embodiment of FIG. 1, the image 21a' of the indication mark appears on the observation screen as a dark point. On the contrary, in this embodiment of FIG. 11 it appears as a bright point. Except for this difference, all the descriptions of adjusting method previously made referring to FIG. 1 is also applicable for the apparatus shown in FIG. 11. Therefore, detailed description of the adjustment procedure as to the embodiment of FIG. 11 is herein omitted.

Figure 12:
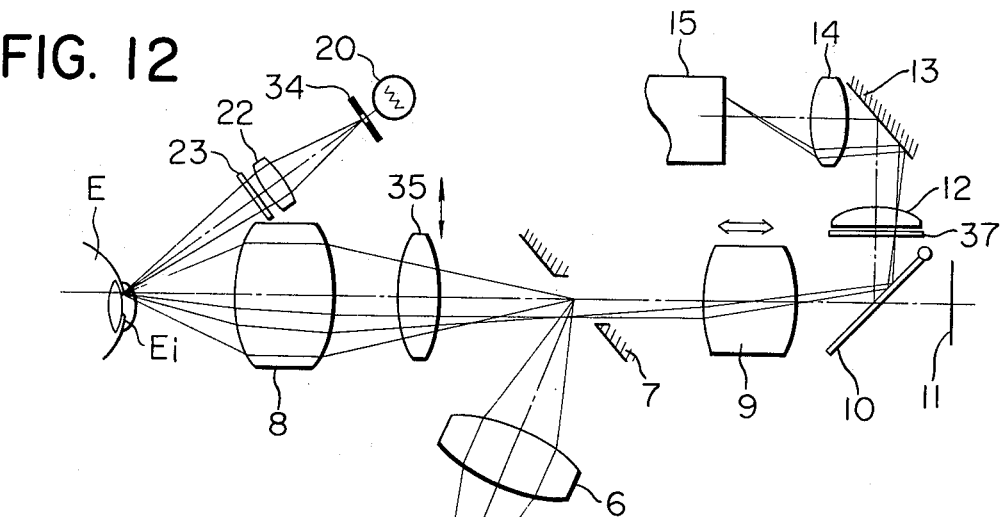
FIG. 12 shows still a further embodiment of the apparatus according to the invention.
Figure 13:
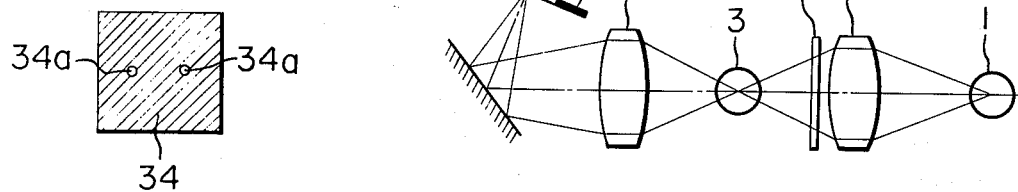
FIG. 13 is a plan view of the chart used in the embodiment shown in FIG. 12.

FIG. 12 shows a further embodiment of the invention. Designated by 34 is a chart provided with small holes 34a. As clearly seen in FIG. 13, the light is allowed to pass the chart only through the holes 34a. The reference numeral 35 designates a positive lens which is removably interposed between the objective and the bored mirror 7. When the positive lens 35 is interposed, the iris Ei and the film surface 11 become substantially conjugated with respect to the lenses 8, 35 and 9 respectively. 37 is a chart which is almost the same as the chart 25 shown in FIG. 1. The chart 37 is disposed adjoining the field lens 12 and is retractable. By interposing the lens 35 and also by switching the light source 1 on, the examiner can observe on the display screen an image of the part of the subject eye around the iris. The images appearing on the display screen correspond to those illustrated in FIGS. 7–10, but the image of indication mark appears as a bright point similar to that in the embodiment of FIG. 11. If the relay lens 9 has a larger moving range for focusing and it is moved toward the image space side to an extended degree, then it will become possible to observe the anterior part of the eye without using the lens 35. However, for this modification it is required to provide a larger spacing preliminary between the relay lens 9 and the flap mirror 10.

Figure 14:
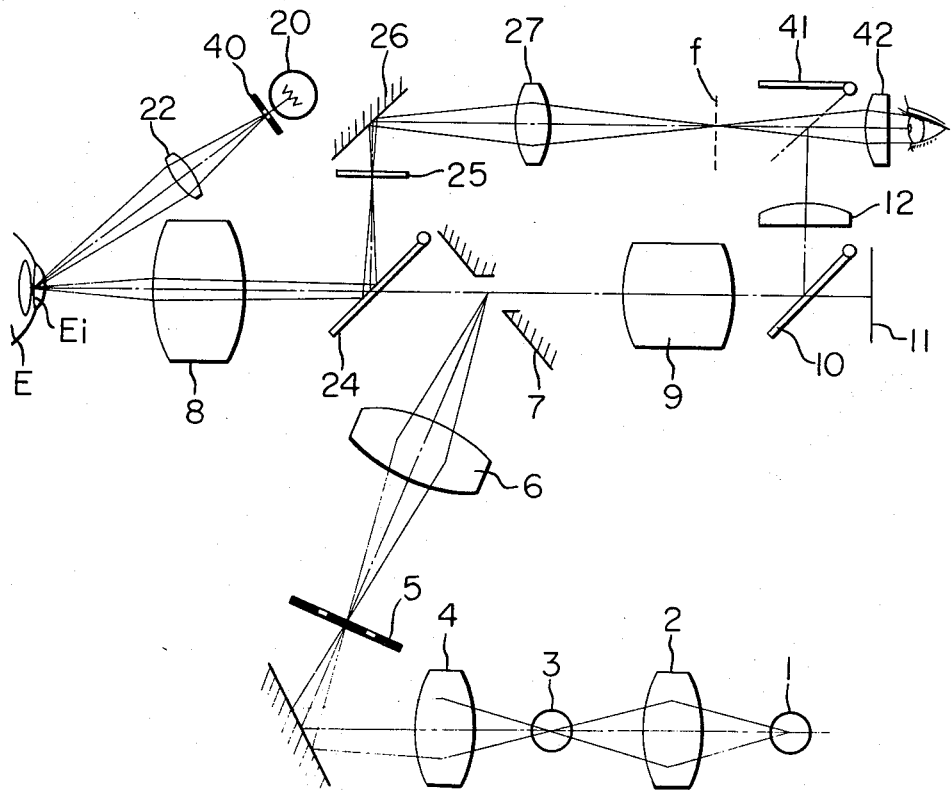
FIG. 14 shows a further embodiment of the apparatus according to the invention.

The description made above relates to the nondilatation type of system. But, the adjustment of working distance is of importance also for the dilatation type of system. FIG. 14 shows an embodiment of the invention relating to a retinal camera of the dilatation system. The arrangement shown in FIG. 14 is substantially the same as that shown in FIG. 1. However, for this embodiment of the apparatus, the infrared filter disposed between the condenser lens 2 and the strobo tube 3 as well as the infrared filter disposed before the projection lens 22 become unnecessary. Designated by 40 is a chart the structure of which is the same as that shown in FIG. 13. The focal plane designated by the broken line f and the chart 25 are conjugate with respect to the lens 27 and therefore an aerial image of the iris is formed on the plane f. Also, the focal plane f and the field lens 12 are disposed substantially conjugated with respect to the mirror surface of a swing mirror 41. Therefore, the examiner viewing through an eyepiece 42 can observe selectively the anterior part of the eye or the fundus of the eye depending upon whether the mirror 41 is in its retracted position or obliquely interposed position.

With the arrangement of the apparatus, when the flap mirror 24 is obliquely interposed, the swing mirror 41 is brought to its retracted position and the light source 20 is switched on, there are given to the examiner such view field as illustrated in FIGS. 7-10. Since a dilatation type retinal camera allows one to take a photograph even in a relatively light room, the provision of a light source for illuminating the anterior part of the eye is not always necessary. But, as in the case of the FIG. 11 embodiment, a separate illumination light source may be provided. Also, instead of a bright indication image, a dark image of indication mark may be projected in the same manner as in the embodiment shown in FIG. 1.

As will be understood from the foregoing, according to the invention, an indication projection system is disposed obliquely relative to an objective optical system opposed to the eye to be examined in such manner that the optical axis of the projection system makes a predetermined inclination with the optical axis of the objective optical system. An indication beam of light in visible range or in other spectral range which does not cause any constriction of the eye is projected directing to the position of the anterior eye part which exhibits a light diffusing property (iris or sclera). While observing an image of the indication through a finder or a cathode ray tube, the examiner adjusts the working distance between the subject eye and the objective optical system. The adjustment is effected by moving the housing to the position at which there is obtained a coincidence of the image of indication and a given position on the picture area (preferably the given position is displayed simultaneously by a mark).

According to the invention described above, not only the adjustments for horizontal and vertical alignments but also the adjustment of working distance can be effected in a simple and accurate manner. Moreover, these adjustments can be carried out independently of each other. This is a particular effect of the present invention. Since as the observing system for the apparatus of the invention there is made use of such optical system the function of which primarily belongs to an ophthalmic apparatus, the apparatus according to the invention is simple in structure and small in size. Further, according to the invention, the observation part of the ophthalmic appparatus can be used advantageously also for the observation during adjustments.

While the invention has been particularly shown and described with reference to the preferred embodiments thereof, it will be understood by those skilled in the art that the foregoing and other changes in form and details can be made therein without departing from the spirit and scope of the invention.

I claim:

1. An ophthalmoscopical apparatus provided with an adjustment system, said apparatus comprising:
    an eye inspecting system including front optical means adapted to be disposed opposite to the eye to be examined;
    a beam transmitting system coupled with said eye inspecting system through beam-direction selecting means;
    an observing device coupled with said beam transmitting system for optically observing the anterior part of the eye to be examined; and
    a projection device comprising means for supporting a chart and optical means for projecting the image of a chart supported by said supporting means onto an eye surface which is spaced a predetermined distance from said front optical means, the optical axis of said projection device being inclined at a predetermined angle with respect to the optical axis of the eye inspection system, said chart supporting means being positioned in said apparatus to support a chart such that the image of said chart appears in a predetermined location on said eye when the distance between said eye and said apparatus is correct.

2. An ophthalmoscopical apparatus according to claim 1, wherein said eye inspecting system comprises rear lens means disposed behind said front optical means, a photographic film disposed behind said rear lens means and an image transmitting system for transmitting the beam emerging from said rear lens means to said observing device.

3. An ophthalmoscopical apparatus according to claim 1, wherein said eye inspecting system includes rear lens means disposed behind said front optical means and said beam transmitting system includes a beam reflector interposed between said front optical means and said rear lens means.

4. An ophthalmoscopical apparatus according to claim 1, wherein said eye inspecting system comprises rear lens means disposed behind said front optical means, a photographic film disposed behind said rear lens means and an image transmitting system for transmitting the beam emerging from said rear lens means to said observing device, and said beam transmitting system includes convergent lens means removably interposed between said front optical means and said rear lens means.

5. An apparatus according to claim 1, wherein said eye inspecting system is optically connected with said observing device, and said beam-direction selecting means includes a beam splitter.

6. An apparatus according to claim 5, wherein said beam splitter includes a partially reflecting mirror.

7. An ophthalmoscopical apparatus provided with an adjustment system, said apparatus comprising:
    a photographic system including objective lens means, a photographic film and an observing device;
    a beam transmitting system adapted for transmitting a beam from said objective lens means to a light receiving surface of said observing device and also for bringing the anterior part of the eye to be examined and said light receiving surface together with said objective lens means into a substantially conjugated relation;
    a projection device comprising means for supporting at least one indication device and optical means for projecting the image of the indication on an eye surface which is spaced a predetermined distance from said objective lens means; and
    means for supporting a chart across the optical path of said beam transmitting system to allow the image of the indication to be checked;
    said indication device being so positioned in said apparatus that the image of said indication appears in a predetermined location on said eye when the distance between said eye and said apparatus is correct.

8. An ophthalmoscopical apparatus according to claim 7, wherein the beam emerging from said indication is of infrared light and said observing device comprises an image pick-up means and an image display device.

9. An ophthalmoscopical apparatus according to claim 7, wherein the beam transmitting system comprises a swing movable reflector adapted in one position to be disposed directly behing said objective lens means and a relay lens means.

10. An ophthalmoscopical apparatus according to claim 7, wherein the beam transmitting system includes a convergent lens means removably disposed directly behind said objective lens means.

* * * * *